US005486460A

United States Patent [19]
Townsend

[11] Patent Number: 5,486,460
[45] Date of Patent: Jan. 23, 1996

[54] METHOD AND TEST KITS FOR IDENTIFYING ALZHEIMER'S DISEASE BY TESTING CEREBROSPINAL FLUID

[75] Inventor: Laurace E. Townsend, Grosse Pointe Pk., Mich.

[73] Assignee: Wayne State University, Detroit, Mich.

[21] Appl. No.: 64,346

[22] Filed: May 20, 1993

Related U.S. Application Data

[63] Continuation of Ser. No. 918,943, Jul. 22, 1992, abandoned, which is a continuation of Ser. No. 32,319, Mar. 30, 1987, abandoned.

[51] Int. Cl.$^6$ .............................. G01N 1/30; G01N 33/48
[52] U.S. Cl. ...................... 435/40.51; 435/975; 436/518; 436/811
[58] Field of Search .............................. 435/29, 7.1, 810, 435/960, 975, 962, 40.5, 40.51; 436/518, 63, 86, 172, 800, 810, 811, 826; 424/3

[56] References Cited

U.S. PATENT DOCUMENTS

| | | | |
|---|---|---|---|
| 4,281,061 | 7/1981 | Zuk et al. | 435/5 |
| 4,666,829 | 5/1987 | Glenner et al. | 435/6 |

FOREIGN PATENT DOCUMENTS 1211194  11/1970  United Kingdom .

OTHER PUBLICATIONS

Z. S. Khachaturian, "Diagnosis of Alzheimer's Disease". Arch. Neurol. 42:1097–1105 (Nov. 1985).
Ph. Schwartz, "Amyloid Degeneration and Tuberculosis in The Aged", Gerontologia, 18:321–362 (1972).
Townsend et al, "Cerebrospinal Fluid Proteins in the Diagnois of Alzheimer's Disease" Neurology 36(4 Suppl. 1): 227 (Apr. 1986).
McKhann et al, "Clinical diagnosis of Alzheimer's disease", Neurology 34:939–944 (Jul. 1984).
Whitmore et al. "Quantitative Cytocentrifugation in the Evaluation of Cerebrospinal Fluid", Acta Cytologica, 26(6):847–850 (Nov.–Dec. 1982).
Townsend et al, "Comparison of Methods for Analysis of CSF Proteins in Patients with Alzheimer's Disease", Neurochemical Pathology, 6:213–229 (Jun. 1987).
Mehta et al, "Paired Helical Filament Antigen in CSF", The Lancet, p. 35 (Jul. 6, 1985).
W. D. Stansfield, *Serology and Immunology*, ch. 8 "Tagged Reagents", pp. 239–276 (MacMillan Publishing Co., New York, 1981).
N. W. Tietz, *Fundamentals of Clinical Chemistry*, pp. 368–374 (W. B. Saunders Company, Philadelphia) 1976.
Kidd et al, "Senile Plaque Amyloid, Paired Helical Filaments and Cerebrovascular Amyloid in Alzheimer'S Disease are all Deposits of the Same Protein", Lancet, p. 278 (Feb. 2, 1985).
Johnson et al, "Improved Technique Utilizing Nonfat Dry Milk for Analysis of Proteins and Nucleic Acids Transferred to Nitrocellulose", Gene Anal. Tech., 1:3–8 (1984).
Iqbal, K., et al, Acta Neuropathol 62:167–177 (1984).
Histology Cell and Tissue Biology, fifth edition, Weiss, L. (editor), Elsevier Biomedical, (1983), pp. 14–15.

*Primary Examiner*—Toni R. Scheiner
*Assistant Examiner*—Patricia A. Duffy
*Attorney, Agent, or Firm*—Ian C. McLeod

[57] ABSTRACT

A method for aid in diagnosing Alzheimer's disease in patients exhibiting the Alzheimer's characteristic dementia is described. Cerebrospinal fluid (CSF) suspected of containing amyloid particles is removed from a patient, living or deceased, concentrated and then stained to determine a count of such particles per unit volume. The method provides a means for confirming Alzheimer's disease.

15 Claims, 1 Drawing Sheet

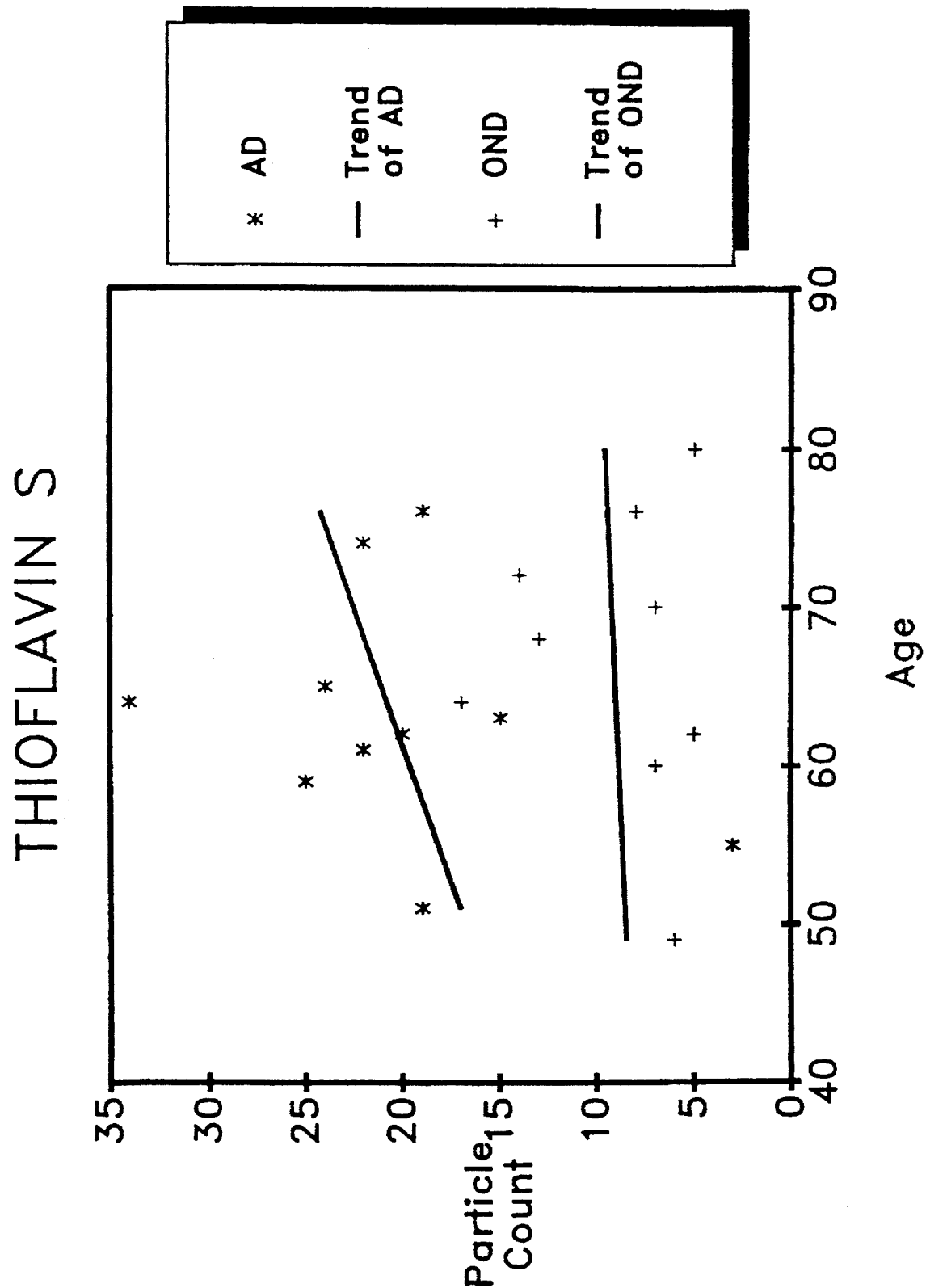

METHOD AND TEST KITS FOR IDENTIFYING ALZHEIMER'S DISEASE BY TESTING CEREBROSPINAL FLUID

This is a continuation of application(s) Ser. No. 07/918,943 filed on Jul. 22, 1992, now abandoned, which is a Continuation of Ser. No. 07/032,319, filed Mar. 30, 1987, now abandoned.

BACKGROUND OF THE INVENTION

(1) Field of the Invention

The present invention relates to a method and test kits for identifying Alzheimer's disease in a living or deceased human, particularly those exhibiting dementia. In particular the present invention relates to a method which can detect abnormally high levels of protein particles including neurofibrillary tangles and neuritic plaque and vascular amyloids in cerebrospinal fluid which are characteristic of Alzheimer's disease.

(2) Prior Art

The only method presently known for positively identifying Alzheimer's disease is by autopsy of patients who have died to obtain brain tissue which is stained with a dye to highlight proteins, including amyloids and neurofibrillary tangles which are characteristic of this disease. At present Alzheimer's disease is not a treatable dementia whereas many types of dementia are treatable. Unfortunately the symptoms of dementia patients with diseases of origin other than Alzheimer's disease are quite similar to Alzheimer's disease and thus there is a need to identify those who have Alzheimer's disease.

The prior work of others has attempted to characterize cerebrospinal fluid (CSF) as a basis for distinguishing Alzheimer's disease. Thus Townsend, L. et al in a poster at the March 1985 meeting of the American Society for Neurochemistry described the use of thioflavine S to stain particles from CSF. This method was not adquately quantitative and therefore could not reliably identify Alzheimer's disease since CSF of normal patients also contains brain amyloids and neurofibrillary tangle proteins. The need for a method which reliably identifies Alzheimer's disease is well known.

OBJECTS

It is therefore an object to provide a method and test kit for identifying Alzheimer's disease protein (brain amyloid and neurofibrillary tangle) particles in CSF. Further it is an object of the present invention to provide a method and test kits which are relatively simple, economical and reliable. These and other objects will become increasingly apparent by reference to the following description and the drawing.

IN THE DRAWINGS

FIG. 1 is a graph showing the presence of protein (brain amyloid and neurofibrillary tangles) particles in concentrated CSF from control, other neurological disease and Alzheimer's disease in living patients.

GENERAL DESCRIPTION

The present invention relates to a method for identifying Alzheimer's disease in a living or deceased human the steps which comprise: providing a sample of cerebrospinal fluid (CSF) containing particles of Alzheimer's disease characteristic protein material from a living or deceased human; staining the particles so as to allow quantification of the particles; and quantifying the particles with the stain, wherein the human with Alzheimer's disease exhibits a significantly higher quantity of the particles per unit volume of CSF than in humans without Alzheimer's disease, including diseases with similar symptoms to Alzheimer's disease.

Further the present invention relates to a method for identifying Alzheimer's disease in a living or deceased human the steps which comprise: providing a sample of cerebrospinal fluid (CSF) containing particles of Alzheimer's disease characteristic protein material from a human; concentrating the CSF sample, to produce a concentrate; adhering a unit of the liquid concentrate on a surface to form a dried concentrate; staining the dried concentrate on the surface with a stain which allows a quantification of the particles; and quantifying the particles on the surface with the stain, wherein the living or deceased human with the Alzheimer's disease exhibits a significantly higher quantity of the particles per unit volume of CSF than humans without Alzheimer's disease, including diseases with similar symptoms to Alzheimer's disease.

Finally the present invention relates to a kit for detecting Alzheimer's disease in a living or deceased human which comprises: a slide means for supporting and quantifying a sample of concentrated cerebrospinal fluid (CSF) containing particles of protein; an adhesive which binds the particles to the slide means when the sample is dried on the slide without interfering with the quantification of the particles; and a stain which selectively stains the particles in the dried sample so that the quantity of the particles can be determined, wherein the human with Alzheimer's disease exhibits a significantly higher quantity of particles per unit volume of CSF than in normal humans without Alzheimer's disease, including diseases with similar symptoms to Alzheimer's disease.

It will be appreciated that the present invention is used in conjunction with a clinical diagnosis of Alzheimer's disease. Other diseases with unrelated symptoms can exhibit high counts of protein particles.

The term CSF includes cerebral spinal fluid from the cisternal region of the brain of alive and deceased patients, since it is relatively simple to obtain from this region and from the lumbar region of living patients. CSF can also be obtained from other regions.

SPECIFIC DESCRIPTION

EXAMPLE 1

The following data particularly shows the use of thioflavin S as a Specific stain for brain amyloid materials and/or neurofibrillary protein tangles in the cerebrospinal fluid (CSF). This stain can be used to quantify brain amyloid and neurofibrillary tangles in the CSF of patients with Alzheimer's disease compared with other neurological controls. Thus, this test can be used as an aid in the diagnosis of Alzheimer's disease.

Thioflavin S staining was used to determine the amounts of brain amyloid and neurofibrillary tangle material present in the CSF of 10 Alzheimer's disease (AD) patients when compared with the CSF of 9 other neurological disease (OND) and normal control patient samples. For each patient, four slides were prepared that each contained the equivalent amount of 80 microliters of unconcentrated CSF. The total number of yellow fluorescent particles found in 12 fields was recorded. AD CSF had significantly elevated numbers of yellow fluorescent particles following thioflavin S staining when compared with OND and normal age-matched controls. Autofluorescence, which was measured spectrophotometrically using a Zonax attachment to the microscope, did not show a significant difference when AD patient CSF was compared with OND control CSF. The data hereinafter shows that AD CSF contains increased amounts of neuritic plaque or cerebrovascular plaque amyloid and/or proteins from neurofibrillary tangles. The results are shown in FIG. 1. The following is a specific description of the staining procedure.

Thioflavin S. Purification

1. A solution of 1% by weight thioflavin S in water was prepared.
2. This solution was centrifuged at 40,000 ×g for 15 minutes.
3. The top lipid layer was removed and discarded.
4. The clear middle layer was removed and stored in a dark container at 5° C.
5. The solution was filtered through a 0.22 Millex Millipore filter immediately before use.

This procedure is important in that it insures the stain does not contribute particles which would provide a false count.

Preparation of Slides

1. Toxoplasmosis slides, eight (8) circle, from Bellco Glass Co. (located at Vineland, N.J. 08360) were used.
2. The slides were washed in 70% by volume ethanol followed by acetone to remove autofluorescent materials.
3. CSF samples were concentrated using an Amicon Minicon™ CS15 concentrator, which is an ultrafiltration device (which is believed to operate on reverse osmosis) with a molecular weight cutoff of 15,000. Appropriate CSF samples, (10 microliters each which had been concentrated Four (4) times), were placed on each slide circle. This step was repeated for a total of 20 microliters of concentrated (80 microliters unconcentrated) CSF.
4. Slides containing the CSF samples were dried on a slide warmer under an inverted dish (to prevent contamination by dust particles).
5. Formal milk (10 microliters), was placed on each slide circle containing CSF and allowed to dry overnight under an inverted dish. The preferred mixture includes 1.0%, a dry skim milk (wt./vol.) and 1.0% formal in, by volume, in water. It is filtered before use. The milk serves as an adhesive. The formaldehyde cross links and aids in adhering the particles from the CSF to the slide.
6. Each slide was covered with the purified thioflavin S solution. This stain was rinsed off after 10 minutes by immersion in 70% by volume ethanol. The slides were washed three additional times in unused 70% by volume ethanol.
7. Each slide was washed in distilled water.
8. The slides were dried on a slide warmer under an inverted dish to prevent dust particle contamination.
9. The slides were viewed under a fluorescent microscope mercury or tungsten lamp with an excitation filter of 450 nm –490 nm and usually a barrier filter of 520 nm.
10. The bright yellow particles from the CSF were counted. CSF samples were carried through the staining procedure in triplicate on separate slides, Twelve fields were counted for each sample slide circle.

As can be seen from the foregoing Example, the CSF solution was concentrated and various low molecular weight contaminants were removed in order to prevent false fluorescence by contaminating particles. Preferably the CSF solution is concentrated at least four (4) times the initial concentration, The concentrating can be by centrifugation of the CSF particles and washing to remove soluble materials or by a molecular sieve which removes water soluble contaminants. The sieve used in the Example to remove contaminants had a molecular weight cut off of less than 15,000 because of availability; however sieves which remove contaminants having a molecuar weight less than about 200,000 can be used. Other means such as filters can be used to remove contaminants. This method enables the dyes to stain only the protein particles in the CSF for accurate counting which has not been possible with the prior art methods.

Various protein revealing stains are well known to those skilled in the art including the fluorescent dyes. In particular, the fluorescent thiazine dyes such as thioflavin T and thioflavin S are preferred. Congo red can by used as the stain with polarized light. This stain produces a greenish bifringence with the protein particles. Other stains can be used so long as they are selective for the protein material. Such stains can include radiolabels for instance. Thus the term "stain" means any composition which directly reacts with the protein particles to produce a color or radiation and including immunostaining methods using ant[bodies. The stains are centrifuged to remove solid impurities, particularly lipids in the thioflavins, and then filtered and stored in the dark.

Various adhesives can be used in place of the milk in the formal milk mixture so long as they do not stain or autofluoresce. A gelatin-chromium potassium sulfate mixture can be used, The sulfate quenches background interference and aids adhesion to a slide, It will be appreciated that a spectrophotometer can be used for detecting stained particles of protein material in CSF. In this method, the CSF-Alzheimer's stained protein particles in a cuvette can be quantified based upon the amount of light from the sample, In the same manner the dried particles on a slide in the described method can be quantified using a Zonex™ attachment and a filter on a light microscope to determine the quantity of light from a sample which relates to the number of particles. Various light sources can be used such as a quartz light. All of these variations will be obvious to one skilled in the art.

It is intended that the foregoing description be only illustrative of the present invention and that the present invention be limited only by the hereinafter appended claims.

I claim:

1. A method for aiding in the diagnosis of Alzheimer's disease after a clinical diagnosis of Alzheimer's type dementia in a living or deceased human the steps which comprise:

(a) providing a sample of cerebrospinal fluid (CSF) suspected of containing amyloid particles from the living or deceased human;
   (b) concentrating the CSF sample, to produce a concentrate of said particles;
   (c) applying a unit of the liquid concentrate with said particles a on a surface;
   (d) drying the concentrate and applying an adhesive so as to bind said particles to the surface;
   (e) staining said particles in the dried concentrate on the surface with a stain which is visible with light from and external light source, where the stain is a thiazine stain which stains said particles; and (f) rinsing excess, non-adherent stain with a solvent which dissolves the excess stain;

(g) counting said particles on the surface by means of said stain, wherein the human with the clinical diagnosis of the Alzheimer's Disease exhibits a higher number of the particles per unit volume of CSF than humans without Alzheimer's Disease and above about 20 particles per 80 microliters of CSF as shown in FIG. 1 with the thioflavin stain.

2. The method of claim 1 wherein the stain is a thioflavin S stain and wherein the surface is a slide.

3. The method of claim 1 wherein the concentrating is by means of centrifugation and washing to separate the particles from other CSF sediment material.

4. A method for aiding in the diagnosis of Alzhemier's disease after a clinical diagnosis of Alzheimer's type dementia in a living or deceased human the steps which comprise:

(a) providing a sample of cerebrospinal fluid (CSF) suspected of containing amyloid particles from the living or deceased human;

(b) concentrating the CSF sample using an ultrafiltration device to remove contaminants and to produce a concentrate of said particles;

(c) providing a unit volume of the concentrate with said particles on a surface with an adhesive;

(d) drying the concentrate and applying an adhesive so as to bind said particles on the surface;

(e) staining said dried concentrate on the surface with a stain which is visible with light from an external light source, wherein the adhesive is not stained by said stain, wherein said stain is a thiazine stain which stains said particles; and (f) rinsing excess, non-adherent stain with a solvent which dissolves the excess stain;

(g) counting said particles on the surface by means of said stain, wherein the human with the clinical diagnosis of the Alzheimer's Disease exhibits a higher number of the particles per unit volume of CSF than humans without Alzheimer's Disease and above about 20 particles per 80 microliters of CSF as shown in FIG. 1.

5. The method of claim 4 wherein the adhesive is a formalin-milk mixture and the stain is thioflavin S.

6. The method of claim 4 wherein said stain is thioflavin S and wherein said particles are counted using the fluorescent microscope having a mercury or halogen tungsten-quartz lamp with an excitation filter of 450–490 nm.

7. The method of claim 4 wherein the CSF sample is concentrated using ultrafiltration which removes contaminants having a molecular weight of less then about 200,000.

8. The method of claim 4 wherein the steps are conducted to avoid dust which stains with the particles to produce a false quantity of particles.

9. The method of claim 4 wherein the stain is thioflavin S and the stain is dispersed in water and then centrifuged to remove solids and stored in the dark prior to use.

10. The method of claim 4 wherein the solvent is an ethanol-water solution which rinses non-particle adherent stain.

11. A kit for aiding in the diagnosis of Alzheimer's disease after a clinical diagnosis of Alzheimer's type dementia in a living or deceased human which comprises:

(a) a slide means for supporting and quantifying a sample of concentrated cerebrospinal fluid (CSF) suspected of containing amyloid particles from the living or deceased human;

(b) a formalin-milk adhesive mixture which binds said particles to the slide means when the sample is dried with the adhesive on the slide without interfering with counting of said particles by staining and so as to permit staining which permits rinsing of excess non-adherent stain with a solvent;

(c) a stain which selectively stains said particles in the dried sample so that a number of said particles can be visibly counted, wherein the stain is a thiazine stain which stains said particles, wherein the human with Alzheimer's Disease exhibits a higher number of particles per unit volume of CSF than in humans without Alzheimer's disease and above about 20 particles per 80 microliters of CSF as shown in FIG. 1; and (d) the solvent for rinsing the excess non-adherent stain.

12. The kit of claim 11 wherein the stain is a thioflavin S stain.

13. The method of claim 1 wherein the step (f) the solvent is 70% ethanol.

14. The method of claim 4 wherein the solvent is 70% ethanol.

15. The kit of claim 11 wherein the solvent is 70% ethanol.

* * * * *

UNITED STATES PATENT AND TRADEMARK OFFICE
CERTIFICATE OF CORRECTION

PATENT NO. : 5,486,460
DATED : January 23, 1996
INVENTOR(S) : Laurace E. Townsend It is certified that error appears in the above-indentified patent and that said Letters Patent is hereby corrected as shown below:

Column 3, line 47, "formal in" should read --formalin--.

Column 4, line 28, "ant[bodies" should read --antibodies--.

Column 4, line 33, "be used, The" should read --be used. The--.

Column 4, line 34, "to a slide," should read --to a slide.--.

Column 4, line 39, "the sample, In" should read --the sample. In--.

UNITED STATES PATENT AND TRADEMARK OFFICE
CERTIFICATE OF CORRECTION

PATENT NO. : 5,486,460
DATED : January 23, 1996
INVENTOR(S) : Laurace E. Townsend It is certified that error appears in the above-indentified patent and that said Letters Patent is hereby corrected as shown below:

Column 4, line 65 (Claim 1), "light from and" should read --light from an--.

Column 6, line 40 (Claim 13), "wherein the" should read --wherein in--.

Signed and Sealed this

Twenty-third Day of July, 1996

BRUCE LEHMAN

*Attest:*

*Attesting Officer*   *Commissioner of Patents and Trademarks*